United States Patent [19]

Sofia

[11] Patent Number: 5,723,501
[45] Date of Patent: Mar. 3, 1998

[54] PHARMACEUTICAL COMPOSITIONS CONTAINING 3-IODO-1,2-PROPANEDIOL HAVING MUCOLYTIC ACTIVITY

[75] Inventor: Robert Duane Sofia, Willingboro, N.J.

[73] Assignee: Carter-Wallace, Inc., NY, N.Y.

[21] Appl. No.: 754,611

[22] Filed: Nov. 20, 1996

[51] Int. Cl.$^6$ ............................................. A61K 31/045
[52] U.S. Cl. ............................................. 514/738
[58] Field of Search ............................................. 514/738

[56] References Cited

PUBLICATIONS

Lu et al., Yao Hsueh Hsueh Pao. (1979), 14 (7), 402–7 Abstract.

*Primary Examiner*—Phyllis G. Spivack
*Attorney, Agent, or Firm*—Kevin B. Clarke

[57] ABSTRACT

The present invention relates to pharmaceutical compositions containing 3-iodo-1,2-propanediol which are effective in increasing the output of thin respiratory tract fluid and liquefying tenacious mucus in the bronchial tree.

4 Claims, No Drawings

PHARMACEUTICAL COMPOSITIONS CONTAINING 3-IODO-1,2-PROPANEDIOL HAVING MUCOLYTIC ACTIVITY

The present invention relates to pharmaceutical compositions containing 3-iodo-1,2-propanediol having mucolytic activity and to a therapeutic method for increasing the output of thin respiratory tract fluid and for liquefying tenacious mucus in the bronchial tree which comprises orally administering a pharmaceutical composition comprising a therapeutically effective amount of 3-iodo-1,2-propanediol in admixture with one or more pharmaceutically acceptable carriers.

There has for a long time past been a widely held belief that iodide is beneficial in the treatment of respiratory conditions, although clinical proof has not been developed to the level required by governmental authorities to gain approval for the use of iodides in such treatment.

Probably, the most widely used mucolytic iodide product has been iodinated glycerol such as described in U.S. Pat. No. 2,872,378. Iodination of glycerol, according to said patent, results in an isomeric mixture of iodinated dimers of glycerol. The precise structures and chemical formula resulting from the iodination of glycerol have not been fully established, however, it is generally accepted to be an isomeric mixture of 67–75% 2-(1-iodoethyl)-1,3-dioxolane-4-methanol or 2,3-(2-iodopropylidenedioxy)propanol and 25–33% of 2-(2-iodoethyl)-1,3-dioxolane-4-methanol or 2,3-(3-iodopropylidenedioxy)propanol.

We have now found that the organic iodide 3-iodo-1,2-propanediol as a singular mucolytic agent is about 90 times as effective as is iodinated glycerol in increasing the output of thin respiratory tract fluid and for liquefying tenacious mucus in the bronchial tree as determined by the tracheal secretion of phenol red in male mice. The stimulated tracheal secretion of phenol red is characteristic of such mucolytic activity.

3-iodo-1,2-propanediol is prepared by reacting 3-chloro-1,2-propanediol with sodium iodide and recovering the desired product in the manner set forth in the following example:

EXAMPLE 1

3-IODO-1,2-PROPANEDIOL 300 g of 3-chloro-1,2-propanediol, 500 g of anhydrous sodium iodide and 2 liters of methyl ethyl ketone are placed in a 5 liter 3 neck round bottom flask equipped with a stirrer, condenser and drying tube. The mixture is stirred with heating to reflux for 24 hours. The sodium chloride formed is then filtered and the filtrate is washed with 2×250 mL acetone. The filtrate is then concentrated at 50° C. in a Rotovap to approximately 500 mL or until no further solvent comes off. The resulting oil and solid is dissolved in 1.5 liters of ethyl acetate and 100 mL of water. The organic layer is separated and washed with 3 100 mL of water containing 10 g of thiosulfate per 100 mL of water. The organic layer is then concentrated at 50° C. in a Rotovap. 15 g of Dowex 50 H⁺ is added and the mixture stirred at room temperature for 48 hours. The mixture is filtered and concentrated at 50° C. in a Rotovap using toluene to remove water. The resulting oil is dissolved in 250 mL chloroform at 50° C. and cooled overnight in a freezer with seeding. The material is filtered and the cake is recovered and washed with 2×125 mL of ice cold chloroform and 50 mL toluene and air dried to constant weight. The yield is 287.9.

The material is recrystallized by dissolving 1250 mL of toluene containing 2% n-butanol at 90° C. 25 g charcoal are added and the material is filtered through celite and rinsed with 150 mL of water containing 10 g thiosulfate per 100 mL of water.

The material is placed in an ice bath with good stirring and refrigerated overnight. The material is filtered and the cake washed with 2×100 mL of water and 3×150 mL toluene. The material is air dried to constant weight the yield is 236 g of 3-iodo-1,2-propanediol as an off-white crystal powder having a purity of 99.5%, organically bound iodine not less than 62.5% w/w and not more than 0.1% w/w free iodine.

The following example demonstrates the effect of iodinated glycerol and 3-iodo-1,2-propanediol on the tracheal secretion of phenol red in male mice.

EXAMPLE 2

Adult male mice weighing 14–40 g were used in this investigation. Animals were acclimatized to the laboratory environment for a minimum of five days prior to use in the experimental procedures. Housing was provided in environmentally controlled quarters in which temperature, humidity and ventilation were regulated based on the needs of the species. Husbandry practices and veterinary care were in accordance with the *Guide for Care and Use of Laboratory Animals* (NIH Publication No. 85-23).

Tracheal secretion in mice, expressed by the amount of phenol red dye secreted into the lumen of the trachea was measured according to the method of Engler and Szelenyi. Male mice were randomly placed into appropriate treatment groups. On each experiment day, one to four mice in a group received orally either vehicle (distilled water or 1% acacia, 0.1 mL/10 g body weight) or a drug. Each drug was tested at a minimum of three different dose levels. Each drug dosage was tested in at least six animals. Drugs were administered orally (0.1 mL/10 g body weight) 30 minutes prior to intraperitoneal injection of phenol red (500 mg/kg: 5% solution in physiological saline, 0.1 mL/10 g body weight). Thirty minutes after phenol red injection the animals were sacrificed by exposure to $CO_2$. The whole trachea was carefully excised and washed in 1.0 mL physiological saline for a period of 30 minutes. Subsequently, 0.1 mL of 1 M NaOH was added to the tracheal washings to stabilize the pH of the lavage fluid. The amount of phenol red was measured photometrically at 546 nM in a Beckman Model 25 spectrophotometer.

The amount of phenol red secreted in the tracheal lumen, expressed in µg/10 g body weight/hr, was determined by the formula of Graziani and Cazzulani:

$$S = s \frac{V}{W} \times 10$$

where:

S=phenol red secreted per 10 g of body weight per hour (µg/10 g/hr).

s=intensity of emission of the phenol red contained in 1.0 mL of tracheal lavage as determined from the standard curve of phenol red (0.5, 1, 5, and 10 µg/mL).

V=volume of the tracheal lavage (1.0 mL).

W=body weight of the mice expressed in grams.

The results were expressed as mean ±S.F.M. Statistical significance was evaluated using the t-test for independent means, where $P<0.05$ is considered to be significant as compared to the appropriate control.

The % increase in tracheal secretion of phenol red by each dose of a drug was determined by using the following formula:

$$\% \text{ Increase} = \frac{T-C}{C} \times 100$$

T=tracheal secretion of phenol red (μg/10 g/hr) in treated mice each day.

C=tracheal secretion of phenol red (μg/10 g/hr) in untreated mice each day.

The line of best fit was calculated from the dose response curve of each drug and the ED50 (mg/kg), i.e. the dose stimulating tracheal secretion of phenol red by 50% over the control level, was determined and 95% confidence limits were also calculated.

Iodinated glycerol, 3-iodo-1,2-propanediol, potassium iodide, N-acetylcysteine and albuterol exerted a dose-dependent increase in the tracheal secretion of phenol red in mice (Table 1). The calculated ED50s (mg/kg, p.o., 30 minutes) were as follows: iodinated glycerol=68.3; 3-iodo-1,2-propanediol=0.75; albuterol=0.18; N-acetylcysteine= 61.8; and potassium iodide=~200. Bromhexine (3, 30 and 100 mg/kg, p.o., 30 minutes) exerted a weak to moderate nondose-related effect (ED50=>100 mg/kg)(Table 1).

The data obtained shows that iodinated glycerol and 3-iodo-1,2-propanediol stimulates tracheal secretion of phenol red which is characteristic of mucolytic activity. 3-iodo-1,2-propanediol is about 90 times as effective as iodinated glycerol in stimulating the tracheal secretion of phenol red in mice.

Albuterol and potassium iodide also stimulated tracheal secretion of phenol red in mice with an oral ED50 of 0.18 and 200 mg/kg, respectively. Earlier, others have reported an oral ED50 of about 4 and 4000 mg/kg for albuterol and potassium iodide, respectively. Bromhexine produced a significant increase in phenol red tracheal secretion only at 100 mg/kg, p.o., but not at 3 or 30 mg/kg. Similarly, others have reported little or no bronchosecretogogue activity of bromhexine at 40 mg/kg, p.o. in mice. The subcutaneous administration of bromhexine at 20–80 mg/kg, 15 minutes before phenol red injection has been reported to exert a dose-dependent increase (10 to 42%) in tracheal secretion in mice.

Expectorant/mucolytic drugs have been known to exert antitussive activity by enhancing the output of respiratory tract fluid. 3-iodo-1,2-propanediol and iodinated glycerol have been found to exert antitussive effect against citric acid (aerosol)-induced coughing responses in guinea pigs and following mechanical or electrical stimulation in the cat. The ability of 3-iodo-1,2-propanediol and iodinated glycerol to enhance tracheal serous secretions may also play a role in their reported antitussive activity in the guinea pig and cat.

The results of foregoing investigation set forth in Table I clearly demonstrates the following:

3-iodo-1,2-propanediol and iodinated glycerol exerted a dose-dependent stimulation of tracheobronchial secretion of phenol red in mice with an oral ED50 of 0.75 and 68.3 mg/kg, respectively. The results demonstrate their mucolytic activity in this animal model system; and The results obtained show that both 3-iodo-1,2-propanediol and iodinated glycerol are effective in stimulating tracheal secretion of phenol red in mice, however, 3-iodo-1,2-propanediol is about 90 times as effective as iodinated glycerol.

TABLE 1

Effect of 3-iodo-1,2-propanediol, iodinated glycerol, Bromhexine, Albuterol, Potassium Iodide and N-acetylcysteine on the Tracheal Secretion of Phenol Red in Mice

| Drug | Oral Dose mg/kg | Phenol Red Secretion (μg/10 g/hr) Control | Treated | % Change | ED50† |
|---|---|---|---|---|---|
| 3-iodo-1,2-propanediol | 0.3 | 0.74 ± 0.08 (14) | 1.02 ± 0.06* (10) | 37.5 ± 8.01 | 0.75 |
|  | 1.0 |  | 1.16 ± 0.13* (11) | 56.55 ± 17.83 | (0.11–5.2) |
|  | 10.0 |  | 1.32 ± 0.16* (11) | 77.36 ± 21.67 |  |
|  | 30.0 |  | 1.56 ± 0.23* (11) | 110.45 ± 31.5 |  |
| iodinated glycerol[1] | 30.0 | 0.99 ± 0.10 (11) | 0.92 ± 0.10 (11) | 0.0 ± 0.0 | 68.3 |
|  | 50.0 | 0.99 ± 0.10 (11) | 1.17 ± 0.06 (11) | 19.8 ± 6.1 | (57.9–80.8) |
|  | 75.0 | 0.64 ± 0.04 (12) | 1.00 ± 0.10* (6) | 61.4 ± 14.9 |  |
|  | 100.0 | 0.99 ± 0.10 (11) | 2.71 ± 0.41* (11) | 172.4 ± 41.6 |  |
| Potassium Iodide | 50.0 | 0.64 ± 0.40 (12) | 0.67 ± 0.07 (11) | 5.1 ± 11.2 | ~200 |
|  | 100.0 | 0.99 ± 0.10 (11) | 1.47 ± 0.15* (11) | 45.8 ± 14.2 |  |
|  | 200.0 | 0.64 ± 0.40 (12) | 0.96 ± 0.10* (11) | 49.1 ± 12.2 |  |
| Bromhexine | 3.0 | 0.99 ± 0.10 (11) | 1.20 ± 0.13 (11) | 20.9 ± 12.9 | >100 |
|  | 30.0 | 0.71 ± 0.08 (7) | 0.67 ± 0.10 (7) | 0 ± 0 |  |
|  | 100.0 | 0.64 ± 0.04 (12) | 0.90 ± 0.10* (10) | 40.6 ± 17.0 |  |
| N-acetylcysteine | 10.0 | 0.71 ± 0.08 (7) | 0.66 ± 0.06 (8) | 2.3 ± 13.2 | 61.8 |
|  | 50.0 | 0.71 ± 0.08 (7) | 1.00 ± 0.08* (7) | 51.6 ± 10.6 | (29.3–130.1) |
|  | 200.0 | 0.74 ± 0.08 (14) | 1.30 ± 0.12* (11) | 75.7 ± 1.5 |  |
| Albuterol | 0.1 | 0.71 ± 0.08 (7) | 0.85 ± 0.08 (8) | 20.5 ± 10.6 | 0.18 |
|  | 0.3 | 0.71 ± 0.08 (7) | 1.30 ± 0.16* (6) | 78.4 ± 22.9 | (0.13–0.27) |
|  | 1.0 | 0.74 ± 0.08 (14) | 1.60 ± 0.09* (11) | 118.6 ± 11.6 |  |

[1]Organidin ® available from Wallace Laboratories, Cranbury, New Jersey
Values are means ± SFM.
*P<0.05 as compared to respective controls.
Numbers in parentheses indicate the number of observations.
†Dose of a drug stimulating tracheal secretion by 50% over the control.

The pharmaceutical compositions according to the present invention are administered by the oral route admixed with the usual compatible carriers, diluents, etc.

The active ingredient, 3-iodo-1,2-propanediol, may be formed into tablets in the usual manner with other ingredients such as corn starch, dibasic calcium phosphate, FD&C Red No. 40, magnesium stearate, microcrystalline cellulose, tribasic calcium phosphate, etc. according to the following formulation:

microcrystalline cellulose mg 3.5
starch mg 1.0
tribasic calcium phosphate mg 12.0
3-iodo-1,2-propanediol mg 30.0
magnesium stearate mg 2.0
dibasic calcium phosphate mg 12.0
FD&C Red #40 mg 0.5

An elixir formulation contains:

3-iodo-1,2-propanediol mg 30
ethyl alcohol 21.75% by volume
and glucose, sodium saccharin, purified water, natural and artificial flavors to yield 60 mg
3-iodo-1,2-propanediol per 5 mL of elixir.

Specific examples have been given illustrating the practice of the present invention, however, the invention is not limited to the specific examples given but is limited only by the scope of the appended claims.

I claim:

1. A pharmaceutical composition having mucolytic activity which comprises a therapeutically effective amount of 3-iodo-1,2-propanediol in admixture with one or more pharmaceutically acceptable carriers and diluents.

2. A pharmaceutical composition as claimed in claim 1 which comprises a tablet.

3. A pharmaceutical composition as claimed in claim 1 which comprises an elixir.

4. A therapeutic method to increase the output of thin respiratory tract fluid and to liquify tenacious mucus in the bronchial tree comprising administering orally a pharmaceutical composition comprising a therapeutically effective amount of 3-iodo-1,2-propanediol in admixture with one or more pharmaceutically acceptable carriers.

* * * * *